(12) United States Patent
Chen et al.

(10) Patent No.: US 7,833,564 B2
(45) Date of Patent: Nov. 16, 2010

(54) ELONGATE MEDICAL DEVICE AND METHOD OF COATING THE SAME

(75) Inventors: Hancun Chen, Maple Grove, MN (US); Scott Larson, Saint Louis Park, MN (US); Jason Romanowski, Richfield, MN (US); Ryan Messer, Rogers, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1022 days.

(21) Appl. No.: 11/509,204

(22) Filed: Aug. 24, 2006

(65) Prior Publication Data
US 2008/0125753 A1    May 29, 2008

(51) Int. Cl.
*B05D 3/02*    (2006.01)
*A61M 25/00*    (2006.01)

(52) U.S. Cl. .................. 427/2.1; 427/2.24; 427/2.28; 427/2.3; 427/372.2; 604/164.13

(58) Field of Classification Search ......... 427/2.1–2.31, 427/154–156
See application file for complete search history.

(56) References Cited

U.S. PATENT DOCUMENTS

| | | | |
|---|---|---|---|
| 5,106,455 A | 4/1992 | Jacobsen et al. | |
| 5,212,000 A * | 5/1993 | Rose et al. | 428/34.7 |
| 5,437,288 A | 8/1995 | Schwartz et al. | |
| 5,772,609 A | 6/1998 | Nguyen et al. | |
| 5,891,507 A | 4/1999 | Jayaraman | |
| 5,902,647 A | 5/1999 | Venkataramani et al. | |
| 6,139,510 A | 10/2000 | Palermo | |
| 6,428,489 B1 | 8/2002 | Jacobsen et al. | |
| 6,766,720 B1 | 7/2004 | Jacobsen et al. | |
| 6,786,876 B2 | 9/2004 | Cox | |
| 2003/0069522 A1 | 4/2003 | Jacobsen et al. | |

FOREIGN PATENT DOCUMENTS

EP        0 500 229 A1    8/1992
WO        01/13984 A2    3/2001

OTHER PUBLICATIONS

U.S. Appl. No. 11/509,210 to Hancun Chen, filed Aug. 24, 2006.

* cited by examiner

*Primary Examiner*—Timothy H Meeks
*Assistant Examiner*—Cachet I Sellman
(74) *Attorney, Agent, or Firm*—Crompton, Seager & Tufte, LLC

(57) ABSTRACT

An elongate medical device including a coating extending over a portion of the elongate medical device having a plurality of apertures formed thereon and a method of applying a coating to such an elongate medical device are disclosed. Prior to applying a coating to the elongate medical device, a removable liquid is dispensed in the plurality of apertures. Subsequently, the removable liquid is removed from the plurality of apertures, leaving the plurality of apertures free of, unobstructed by, or otherwise not filled with the coating.

28 Claims, 11 Drawing Sheets

US 7,833,564 B2

ELONGATE MEDICAL DEVICE AND METHOD OF COATING THE SAME

TECHNICAL FIELD

The invention generally relates to medical devices for insertion in body lumens, such as the vasculature, having a plurality of apertures or flexibility regions and methods of applying a coating to medical devices having a plurality of apertures or flexibility regions.

BACKGROUND

Elongated medical devices are commonly used to facilitate navigation through and/or treatment within the anatomy of a patient. A wide variety of elongate medical devices have been developed for intracorporeal medical use, for example, intravascular use. Some of these devices include catheters and guidewires. As the anatomy of a patient may be very tortuous, it is often desirable to combine a number of performance features in such devices. For example, it is sometimes desirable that the device have a relatively high level of pushability and torqueability, particularly near its proximal end. It is also sometimes desirable that a device be relatively flexible, particularly near its distal end. A number of different elongated medical device structures and assemblies are known, each having certain advantages and disadvantages. However, there is an ongoing need to provide alternative medical devices and manufacturing methods for producing elongate medical devices.

SUMMARY

The invention provides several alternative designs, materials, and methods of manufacturing alternative medical device structures and assemblies.

Accordingly, one example embodiment is directed to an elongate medical device including an elongate member having an outer surface and a plurality of apertures formed about the outer surface along at least a portion of the elongate member. The elongate medical device includes a coating extending over at least part of the portion of the elongate member including the plurality of apertures, such that the plurality of apertures are generally free of, unobstructed by, or otherwise not filled with the coating. In some embodiments, the coating includes a plurality of openings corresponding to the plurality of apertures.

Another example embodiment is directed to a method of applying a coating to an elongate medical device. The method includes dispensing a removable liquid, such as a solvent, in the plurality of apertures formed in the outer surface of an elongate member. A coating material may then be applied to the elongate medical device including the portion of the elongate medical device which includes the plurality of apertures filled with the removable liquid. The removable liquid may then be removed from the plurality of apertures, leaving the plurality of apertures free of, unobstructed by, or otherwise not filled with the coating material.

BRIEF DESCRIPTION OF THE DRAWINGS

The invention may be more completely understood in consideration of the following detailed description of various embodiments in connection with the accompanying drawings, in which.

Figure 1:
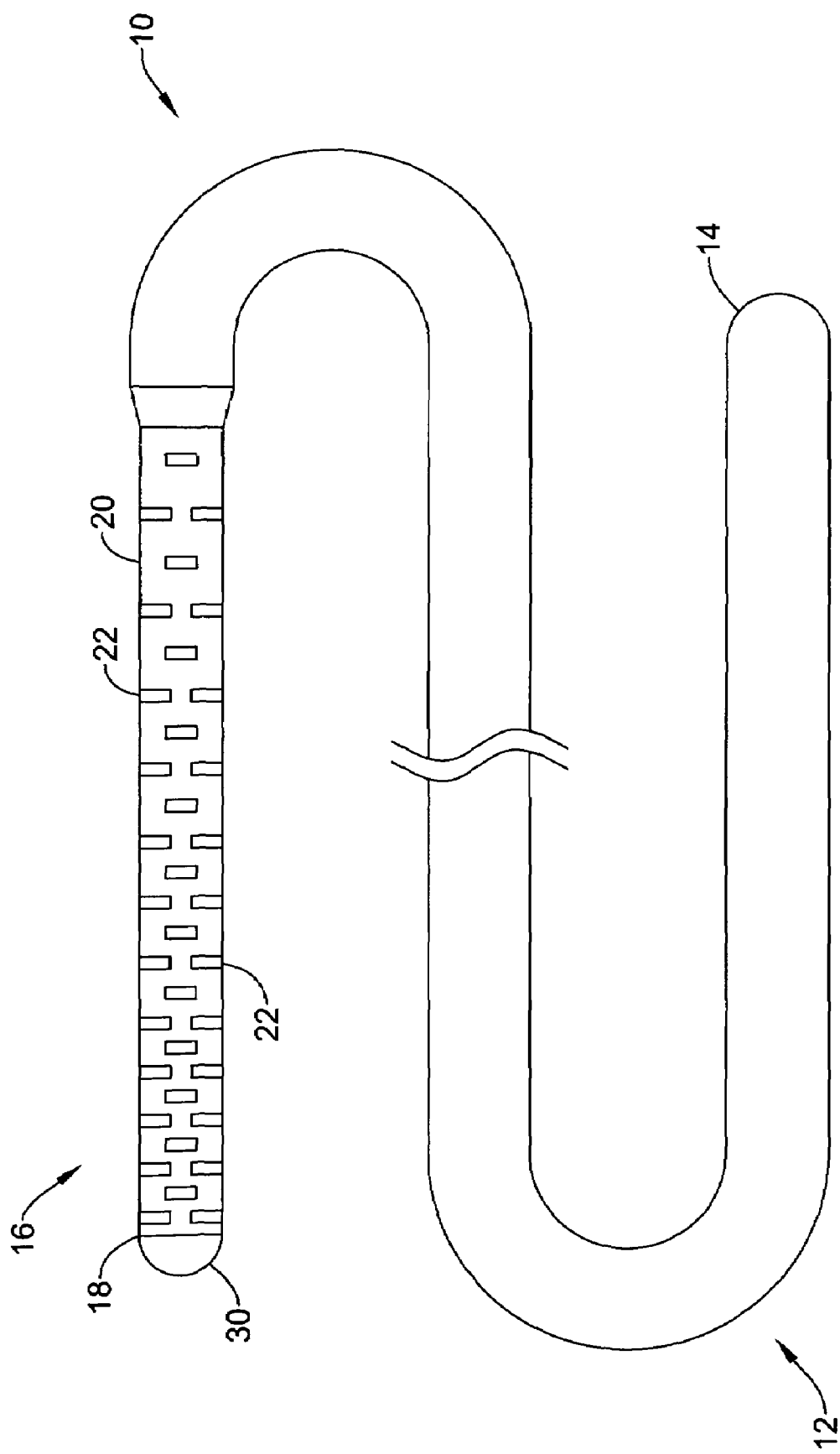
FIG. 1 is a plan view of an illustrative elongate medical device in accordance with one example embodiment, shown as a guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the Figures, an exemplary elongate medical device is shown in FIG. 1 as a guidewire 10. It is noted that although a guidewire 10 is shown, the invention is not intended to be limited to guidewires. Other elongate medical devices, for example, catheters, may incorporate similar characteristics. The guidewire 10 includes a proximal region 12 proximate a proximal end 14 and a distal region 16 proximate a distal end 18 of the guidewire 10. The lengths of the regions 12/16 (and/or the length of the guidewire 10) are typically dictated by the length and flexibility characteristics desired in the final medical device. For example, in some embodiments, the proximal region 12 may have a length in the range of about 20 to about 300 centimeters or more, and the distal region 16 may have a length in the range of about 3 to about 50 centimeters or more. As these lengths are only illustrative, it can be appreciated that in other embodiments alterations in the length of the regions 12/16 can be made without departing from the spirit of the invention.

A portion of the guidewire 10, such as the distal region 16 includes an elongate member 20 including a plurality of apertures 22 to provide a degree of flexibility to the distal region 16 of the guidewire 10. In some embodiments, the elongate member 20 may extend only through the distal region 16. Thus, the elongate member 20 may have a length in the range of about 3 to about 50 cm. However, in other embodiments, the elongate member 20 may extend a majority of the length of the guidewire 10 or substantially the entire length of the guidewire 10. The elongate member 20 will be described in greater detail while referring to FIG. 2.

A distal tip member 30 may be disposed at the distal end 18 of the guidewire 10. The distal tip member 30 may accommodate for accurate movement through the tortuous vasculature of the human body. The distal tip member 30 may comprise any suitable structure. For example, the distal tip member 30 may include a solder ball or a polymeric member coupled to the distal end 18 of the guidewire 10. In some embodiments, the distal tip member 30, or another portion of the guidewire 10, may be doped with, coated with or plated with, made of, or otherwise include a radiopaque material in order to impart a suitable degree of radiopacity to provide visualization of the guidewire 10 on a fluoroscopy screen or other imaging device.

Figure 2:
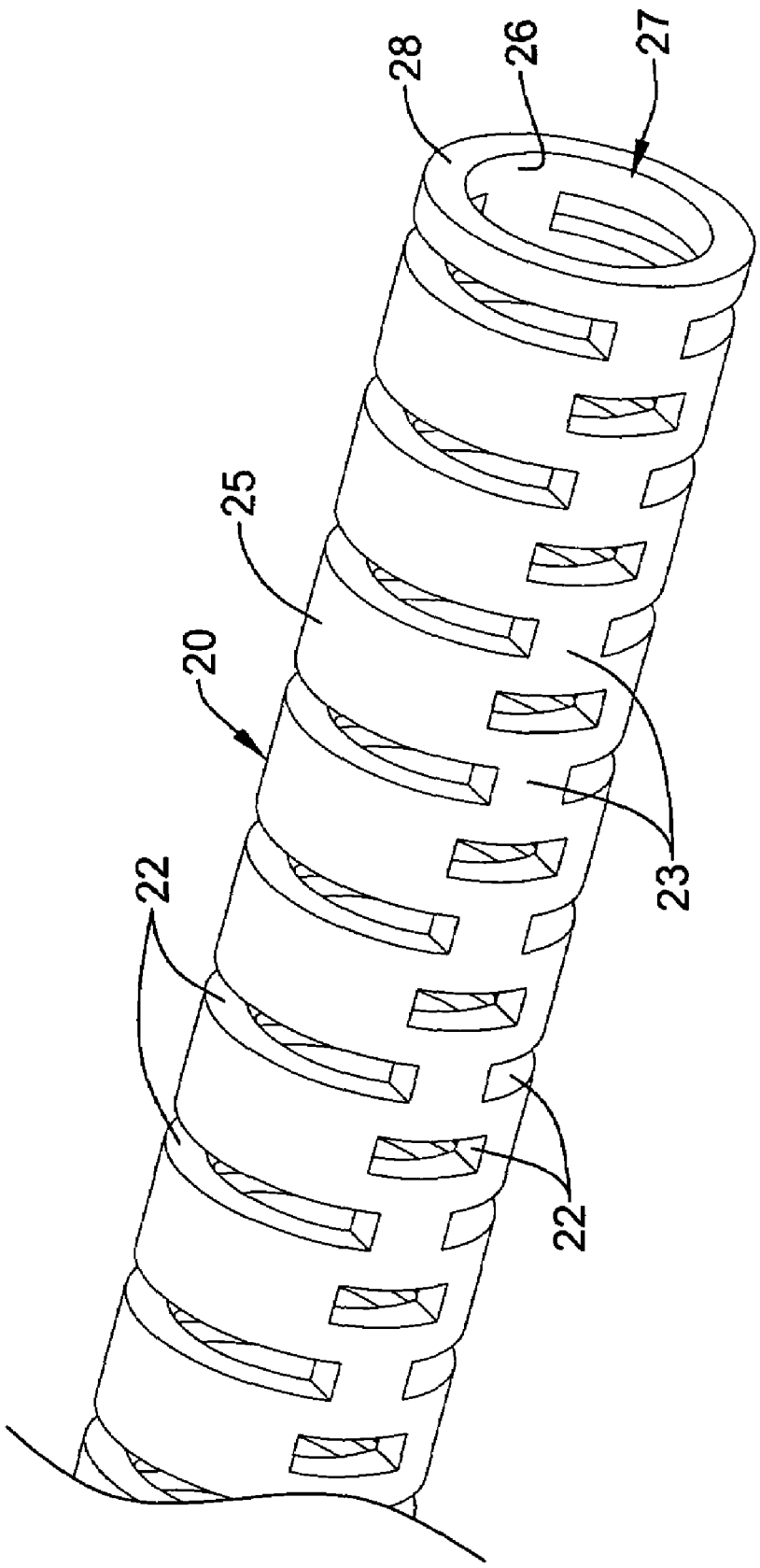
FIG. 2 is a perspective view of a portion of an elongate member of the illustrative guidewire of FIG. 1.
Figure 7:
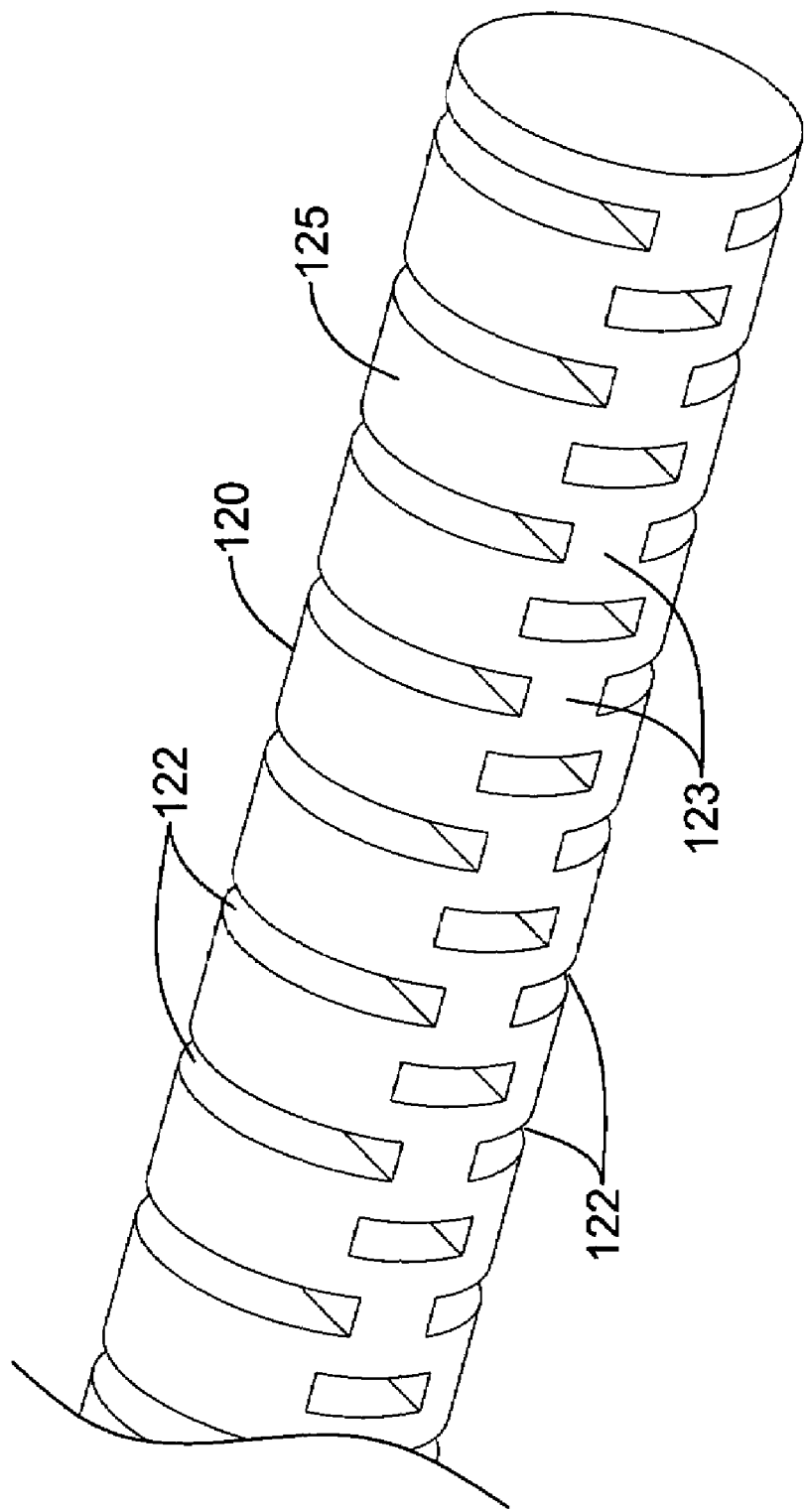
FIG. 7 is a perspective view of a portion of an elongate member of another illustrative elongate medical device.

Now referring to FIG. 2, the elongate member 20 of the guidewire 10 will be further described. The elongate member 20 includes an outer surface 25 and an inner surface 26 defining a lumen 27 therethrough. Thus, the elongate member 20 may be a thin-walled tubular structure having an annular sidewall 28. Although the elongate member 20 is described in FIG. 2 as having a lumen 27, in other embodiments, the elongate member 20 (as shown in FIG. 7) may be a solid member having a solid cross-section, thus not including a lumen, such as the lumen 27.

In some embodiments, the elongate member 20 may have a length in the range of about 3 cm to about 50 cm or in the range of about 5 cm to about 20 cm. However, it should be understood that these lengths are given by way of example only, and that it is contemplated that other lengths may be used as desired.

The elongate member 20 may be made from any suitable material including metals, metal alloys, polymers, or any other suitable material. Some examples of suitable metals and metal alloys include stainless steel, such as 304V, 304L, and 316L stainless steel; alloys including nickel-titanium alloys such as linear elastic or superelastic (i.e., pseudoelastic) nitinol; nickel-chromium alloys; nickel-chromium-iron alloys; cobalt alloys; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 825; or the like; or other suitable materials. Some examples of suitable polymeric materials may include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, and their copolymers, or mixtures, blends or combinations thereof, or polymer/metal composites, etc.

The elongate member 20 includes a plurality of apertures 22, such as grooves, cuts, slits, slots, or the like, formed in a portion of, or along the entire length of, the elongate member 20 in order to enhance the lateral flexibility and bendability of the distal region 16 of the guidewire 10 while retaining the ability to transmit torque and pushing forces from the proximal region 12 to the distal region 16. The apertures 22 can be formed in essentially any known manner. For example, the apertures 22 can be formed by methods such as micro-machining, saw-cutting, laser cutting, grinding, milling, casting, molding, chemically etching or treating, or other known methods, and the like. In some such embodiments, the structure of the elongate member 20 is formed by cutting and/or removing portions of the tube to form the apertures 22.

In some embodiments, the apertures 22 can completely penetrate the sidewall 28 of the elongate member 20 such that there is fluid communication between the lumen 27 and the exterior of the elongate member 20 through the apertures 22. In some embodiments, the apertures 22 may only partially extend into the sidewall 28 of the elongate member 20, either on the inner surface 26 or the outer surface 25 thereof. Some other embodiments may include combinations of both complete and partial apertures 22 through the structure of the elongate member 20. The shape and size of the apertures 22 can vary, for example, to achieve the desired characteristics. For example, the shape of apertures 22 can vary to include essentially any appropriate shape, such as square, round, rectangular, pill-shaped, oval, polygonal, elongate, irregular, or the like, and may include rounded or squared edges, and can be variable in length and width, and the like.

Additionally, the spacing, arrangement, and/or orientation of the apertures 22, or in some embodiments, associated spines or beams 23 that may be formed, can be varied to achieve the desired characteristics. For example, the apertures 22 may be oriented helically around the elongate member 20, transverse to the longitudinal axis of the elongate member 20, or any other arrangement. Additionally, the number or density of the apertures 22 along the length of the elongate member 20 may be constant or may vary, depending upon the desired characteristics. For example, the number or proximity of the apertures 22 to one another near one end of the elongate member 20 may be high, while the number or proximity of apertures 22 to one another near the other end of the elongate member 20 may be relatively low and/or non existent, or vice versa. For example, in the embodiment shown in FIG. 1, the distal portion of the elongate member 20 includes a plurality of apertures 22 having a relatively high density relative to the plurality of apertures 22 located in a more proximal portion of the elongate member 20. As such, the more distal portion of the elongate member 20 can have a greater degree of lateral flexibility relative to the more proximal portion. The density of the apertures 22 can vary gradually or in a stepwise fashion over the length of the elongate member 20. And as suggested above, certain portions of the elongate member 20 may not include any such apertures.

As suggested above, the apertures 22 may be formed such that one or more spines or beams 23 are formed in the elongate member 20. Such spines or beams 23 could include portions of the elongate member 20 that remain after the apertures 22 are formed in the body of the elongate member 20. For example, the spines or beams 23 may be portions of the annular sidewall 28 that remain after the apertures 22 are formed in the sidewall 28 of the elongate member 20. Such spines or beams 23 may act to maintain a relatively high degree of torsional stiffness, while maintaining a desired level of lateral flexibility. In some embodiments, some adjacent apertures 22 can be formed such that they include portions that overlap with each other about the circumference of the elongate member 20. In other embodiments, some adjacent apertures 22 can be disposed such that they do not necessarily overlap with each other, but are disposed in a pattern that provides the desired degree of lateral flexibility. Additionally, the apertures 22 can be arranged along the length of, or about the circumference of, the elongate member 20 to achieve desired properties. For example, the apertures 22 can be arranged in a symmetrical pattern, such as being disposed essentially equally on opposite sides about the circumference of the elongate member 20, or equally spaced along the length of the elongate member 20, or can be arranged in an increasing or decreasing density pattern, or can be arranged in a non-symmetric or irregular pattern.

Figure 3:
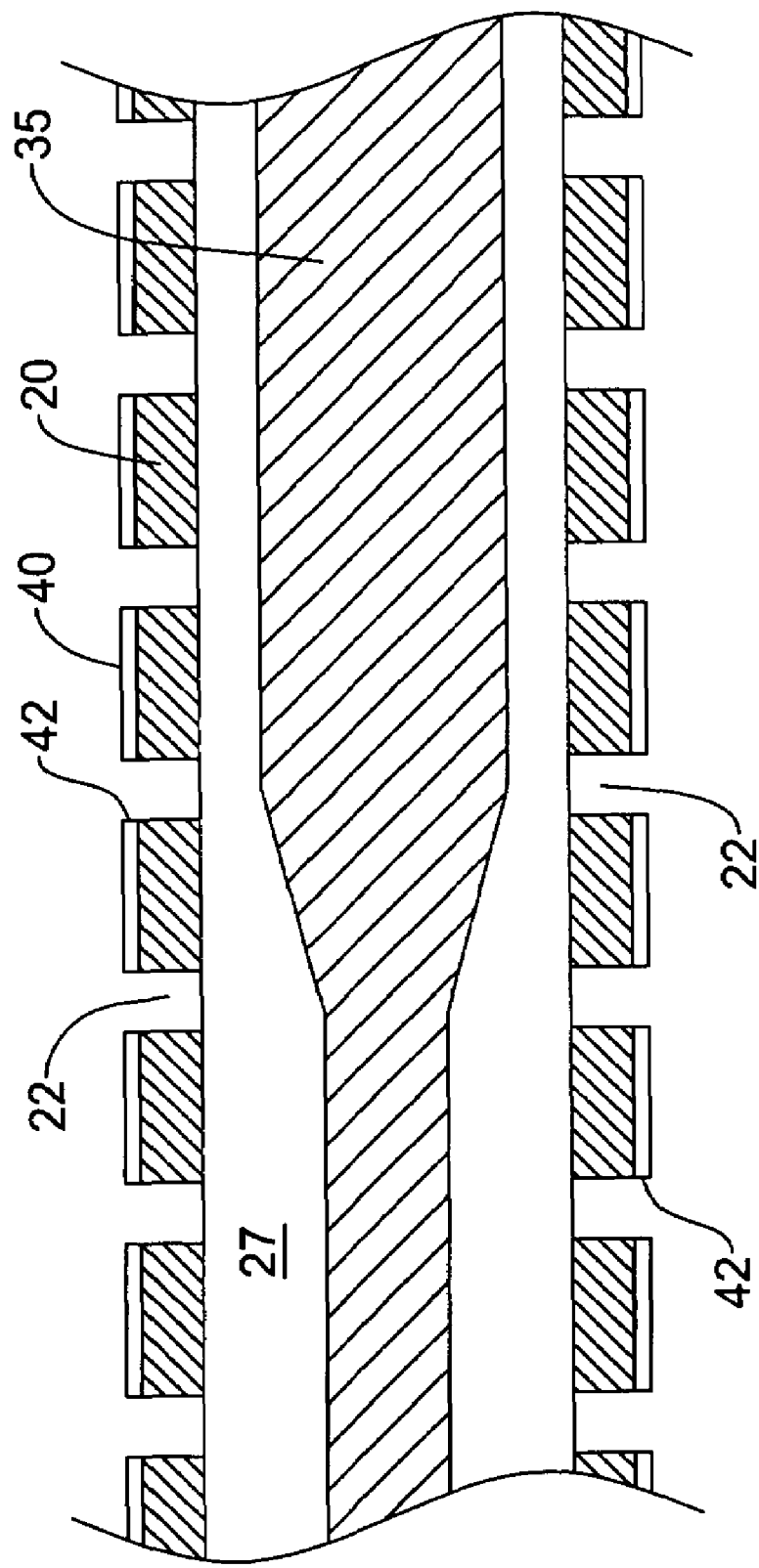
FIG. 3 is a cross-sectional view of a portion of the illustrative guidewire of FIG. 1 including an outer coating.

FIG. 3 is a cross-sectional view of a portion of the guidewire 10 shown in FIG. 1. As shown in FIG. 3, the guidewire 10 may include a core member 35 extending through at least a portion of the elongate member 20. Thus, the core member 35 may be positioned in the lumen 27 of the elongate member 20. For example, the core member 35 may be concentrically or eccentrically disposed within the lumen 27 of the elongate member 20. In some embodiments, the core member 35 may extend from the proximal end 14 of the guidewire 10 into the distal region 16 of the guidewire 10 and/or substantially to the distal end 18 of the guidewire 10. The core member 35 may be made from any suitable material including metals, metal alloys, polymers, or any other suitable material. For example, the core member 35 may include, but is not limited to, any of the materials listed above with reference to the elongate member 20.

As shown in FIG. 3, the core member 35 may include one or more tapers or tapered regions. In some embodiments the core member 35 may be tapered and have an initial outside size or diameter that can be substantially the same as the inside diameter of the elongate member 20, which then tapers to a reduced size or diameter. For example, in some embodiments, the core member 35 can have an initial outside diameter that is in the range of about 0.255 mm to about 0.510 mm that tapers to a diameter in the range of about 0.0255 mm to about 0.1275 mm. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. Although FIG. 3 depicts the core member 35 as being tapered, it can be appreciated that in other embodiments the core member 35 may not include a tapered region. The number, arrangement, size, and length of the narrowing and constant diameter portions of the core member 35 can be varied to achieve the desired characteristics, such as flexibility and torque transmission characteristics. The narrowing and constant diameter portions as shown in FIG. 3 are not intended to be limiting, and alterations of this arrangement can be made without departing from the spirit of the invention.

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing the core member 35 during the grinding process. In some embodiments, the core member 35 can be centerless ground using a Royal Master HI-AC centerless grinder.

Although not shown in FIG. 3, the core member 35 typically may be welded, soldered, brazed, adhesive bonded, or otherwise attached to the elongate member 20 at one or a plurality of locations along the core member 35 and/or at one or a plurality of locations along the elongate member 20. For example, the proximal end and/or the distal end of the elongate member 20 may be attached to the core member 35 at a location proximate the proximal and/or distal ends of the elongate member 20. Additionally or alternatively, the elongate member 20 may be attached to the core member 35 at one or a plurality of intermediate locations intermediate the ends of the elongate member 20.

A coating 40, such as a polymeric coating, may be disposed on the outer surface 25 of the elongate member 20, or a portion thereof. The coating 40 may be disposed on the elongate member 20 and/or other portions of the guidewire 10. For example, the coating 40 may extend a majority of the length or substantially the entire length of the guidewire 10, or the coating 40 may extend only through the distal region 16 of the guidewire 10. In some embodiments, the coating 40 is at least disposed on the outer surface 25 of a portion of the elongate member 20 including the plurality of apertures 22.

The coating 40 may include a plurality of openings 42 corresponding to the plurality of apertures 22 of the underlying portion of the elongate member 20. Thus, in some embodiments, the plurality of apertures 22 of the elongate member 20 are free of unobstructed by, or otherwise not filled with the material forming the coating 40. By not filling the apertures 22 of the elongate member 20 with the coating material of the coating 40, the lateral flexibility of the portion of the elongate member 20 including the plurality of apertures 22 is not diminished.

The coating 40 may be a lubricious, a hydrophilic, a hydrophobic, a protective, a medicated, or other type of coating. Suitable materials for the coating 40 are well known in the art and may include silicone, polysulfones, polyfluorocarbons (such as TEFLON), polyolefins such as polyethylene, polypropylene, polyesters (including polyamides such as nylon), polyurethanes, polyarylene oxides, polyvinylpyrolidones, polyvinylalcohols, hydroxyl alkyl cellulosics, algins, saccharides, caprolactones, and the like, and mixtures and combinations thereof. Suitable coating materials may be blended among themselves or with formulated amounts of water insoluble compounds (including some polymers) to yield coatings with suitable lubricity, bonding, and solubility. Some other examples of such coatings and materials used to create such coatings can be found in U.S. Pat. Nos. 6,139,510 and 5,772,609, which are incorporated herein by reference.

In disposing the coating material on the elongate member 20 to form the coating 40, the coating material may be dissolved, suspended in, or otherwise mixed with a solvent. Some preferred solvents include water (such as deionized water), alcohol (e.g., isopropyl alcohol (IPA) and ethyl alcohol), ethers (e.g., methanol, propanol, isopropanol, and ethanol), toluene, N-methyl-2-pyrrolidone (NMP), tetrahydrofuran, methylene dichloride, methylethylketone, dimethylacetate, ethyl acetate, and their mixtures and combinations thereof. Subsequent to applying the coating material on the elongate member 20, the solvent may evaporate, or otherwise dissipate, leaving the coating material to form the coating 40.

Figure 4:
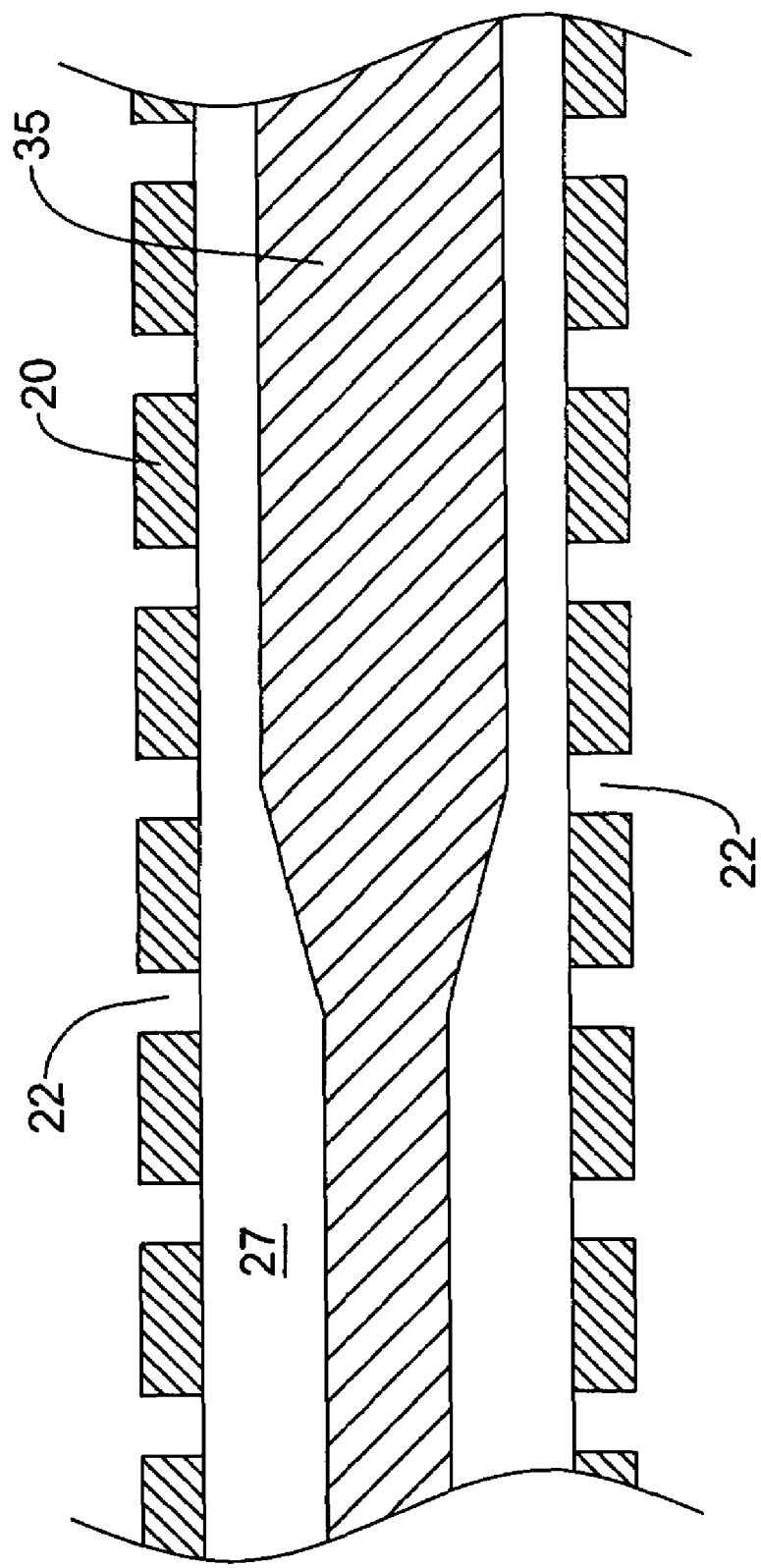
FIGS. 4-6 are cross-sectional views depicting an illustrative method of applying a coating to a portion of an elongate medical device.

A method of applying the coating 40 onto the outer surface 25 of the elongate member 20 will now be discussed in connection with FIGS. 4-6. In FIG. 4, a portion of the guidewire 10 including the elongate member 20 having a plurality of apertures 22 is shown absent a coating or outer layer. The core member 35 is shown extending through the elongate member 20. However, in some embodiments, the core member 35 may be positioned through the elongate member 20 subsequent application of a coating 40, or in other embodiments, the guidewire 10 may be absent a core member 35.

Figure 5:
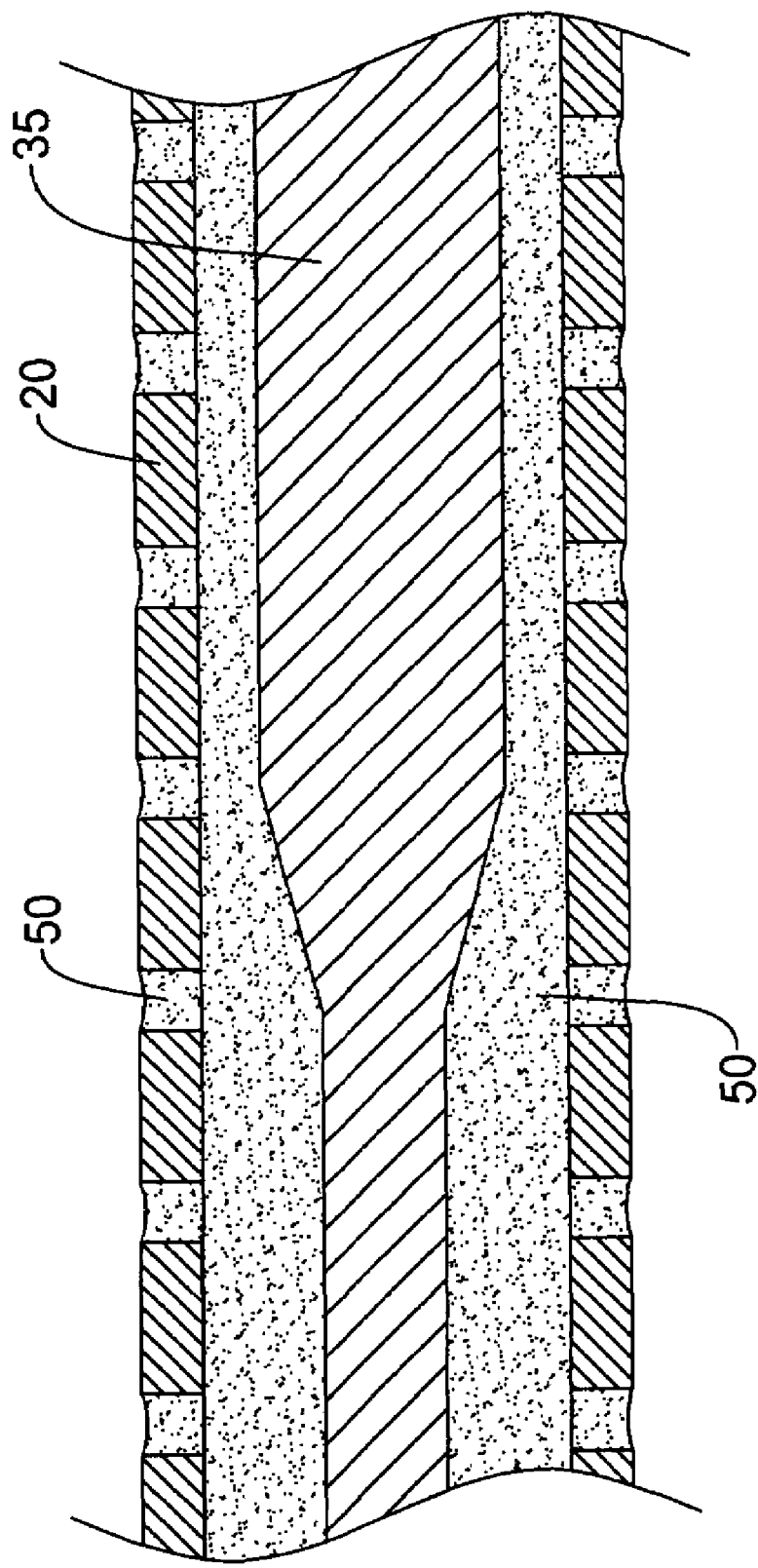

Now referring to FIG. 5, prior to applying the coating 40 to the guidewire 10, a removable material such as liquid 50 may be disposed or dispensed in the plurality of apertures 22 of the elongate member 20, or a portion thereof. The removable liquid 50 may be disposed or dispensed in the apertures 22 of the elongate member 20 in a variety of ways, such as a dipping technique, a spraying technique, or a wiping technique, for example. In some embodiments wherein the elongate member 20 includes a lumen 27, such as shown in FIG. 5, the removable liquid 50 may also be disposed in the lumen 27. The removable liquid 50 may be retained in the plurality of apertures 22 and/or the lumen 27 by capillary action or capillarity and/or surface tension. Capillarity is the ability of a narrow tube to draw a liquid upwards against the force of gravity. Capillarity occurs when the adhesive intermolecular forces between the removable liquid 50 and adjacent surface of the elongate member 20 are stronger than the cohesive intermolecular forces within the removable liquid 50. Equilibrium is established when the adhesive forces equal the cohesive forces. Surface tension and/or adhesive forces hold the removable liquid 50 in the plurality of apertures 22 and/or lumen 27.

The height, h, in meters of a column of liquid in a tubular member drawn upward due to capillarity is given by the formula of:

$$h = \frac{2T\cos\theta}{\rho g r}$$

where:
T=interfacial surface tension (N/m)
θ=contact angle
ρ=density of liquid (kg/m$^3$)
g=acceleration due to gravity (m/s$^2$)
r=radius of tube (m)

Due to the dimensional characteristics of the elongate member 20, it has been determined that the column height of the removable liquid 50 in the lumen of a tubular member which may be used in some embodiments of a guidewire may reach 2, 3, 4, 6 or 8 meters or greater.

In some embodiments, the removable liquid 50 may be a solvent. Some preferred solvents include water (such as deionized water), alcohol (e.g., isopropyl alcohol (IPA) and ethyl alcohol), ethers (e.g., methanol, propanol, isopropanol, and ethanol), toluene, N-methyl-2-pyrrolidone (NMP), tetrahydrofuran, methylene dichloride, methylethylketone, dimethylacetate, ethyl acetate, and their mixtures and combinations thereof. In some embodiments, it may be desirable that the solvent comprising the removable liquid 50 is the same as, or otherwise compatible with, the solvent utilized in the coating material solution, suspension, or mixture as described above. In such embodiments, the compatibility of the removable liquid 50 and the coating material solution, suspension, or mixture may help ensure formation of a continuous coating 40 on the outer surface 25 of the elongate member 20.

Figure 6:
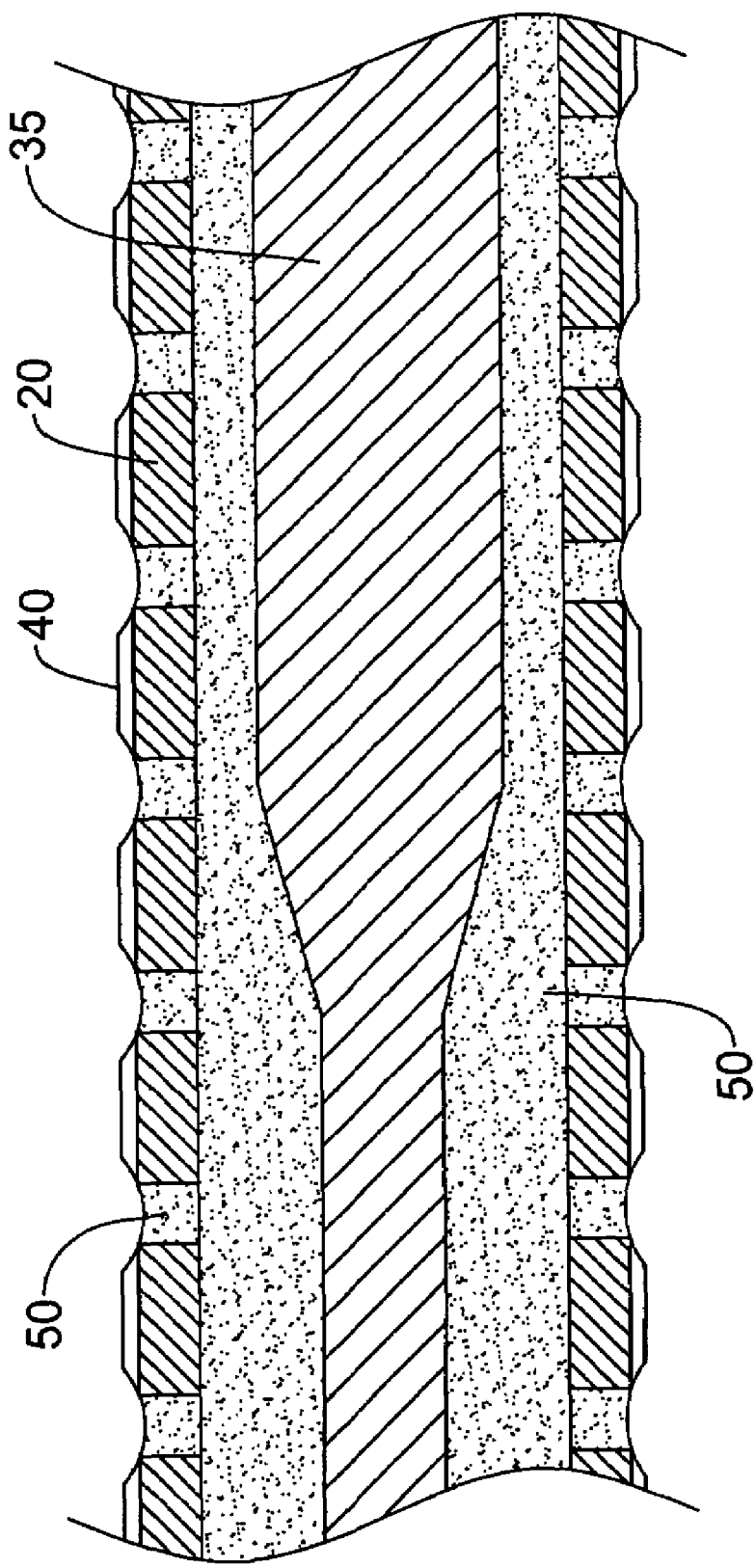

Now referring to FIG. 6, after the plurality of apertures 22 and/or the lumen 27 are filled with the removable liquid 50, the coating material forming the coating 40 may be applied to the elongate member 20. The coating material forming the coating 40 may be applied to the elongate member 20 by any of a variety of methods. For example, the coating material may be applied by spraying a solution or suspension of the coating material onto the elongate member 20, or the coating material may be applied by dipping the elongate member 20 into a solution or suspension of the coating material. In other embodiments, the coating 40 may be applied through an electro-coating process, an aqueous dispersion process, or a non-aqueous dispersion process, for example.

Because the plurality of apertures 22 are filled with the removable liquid 50 prior to the application of the coating 40, the coating material is prevented from entering, obstructing, and/or filling the plurality of apertures 22 of the elongate member 20. The coating material may provide a uniform coating 40 on the outer surface 25 of the elongate member 20, while leaving the plurality of apertures 22 generally free of, unobstructed by, or otherwise not filled with the coating material.

After the coating process is complete, the guidewire 10, or at least the portion of the guidewire 10 including the coating 40 may undergo a process of removing the removable liquid 50 from the apertures 22 and/or the lumen 27 of the elongate member 20 and/or curing the coating 40. For, example, an oven (or other chamber used for heating and/or drying) may be used to cure the coating 40 and/or evaporate or dissipate the removable liquid 50. In some embodiments, evaporation operations may be conducted using a heating chamber suitable for maintaining an environment of between about 75° C. to about 110° C. However, other temperature environments are possible. In some embodiments, ultraviolet (UV) light sources, or other radiation sources, may be used to cure the coating 40 and/or evaporate or dissipate the removable liquid 50. Alternatively, the removable liquid 50 may be removed from the apertures 22 and/or the lumen 27 by dissipation through natural evaporation (e.g., at room temperature) and/or expulsion such as with a vacuum or other expulsion means.

Subsequent to the removal of the removable liquid 50 from the plurality of apertures 22 and/or the lumen 27, the apertures 22 are generally free of, unobstructed by, or otherwise not filled with, the coating 40, as shown in FIG. 3. Thus, contrary to previous coatings which fill, bridge, or otherwise obstruct the apertures 22, the flexibility imparted on the guidewire 10 from the inclusion of the plurality of apertures 22 may be retained, yet the guidewire 10 may possess the benefits attributed to the inclusion of the coating 40.

Another embodiment of a portion of a guidewire including an elongate member 120 having a solid cross-section is shown in FIG. 7. The elongate member 120 may be made from any suitable material including metals, metal alloys, or polymers, such as, but not limited to, those materials listed above regarding the elongate member 20, or any other suitable material. As with the elongate member 20, the elongate member 120 includes a plurality of apertures 122, such as grooves, cuts, slits, slots, or the like, formed in a portion of, or along the entire length of, the elongate member 120 in order to enhance the lateral flexibility and bendability of the elongate member 120 while retaining the ability to transmit torque and pushing forces through the elongate member 120. The plurality of apertures 122 may be formed about the outer surface 125 of the elongate member 120 and extend inward from the outer surface 125. The apertures 122 may be formed by any suitable method, such as, but not limited to, those methods identified above regarding the formation of the apertures 22. Similar to the apertures 22 discussed above, the spacing, arrangement, and/or orientation of the apertures 122 may be selected as desired.

In forming the plurality of apertures 122, one or a plurality of spines or beams 123 are formed in the elongate member 120. Such spines or beams 123 include portions of the elongate member 120 remaining after the apertures 122 are formed in the body of the elongate member 120. Such spines or beams 123 may act to maintain a relatively high degree of torsional stiffness, while maintaining a desired level of lateral flexibility to the elongate member 120.

Figure 8:
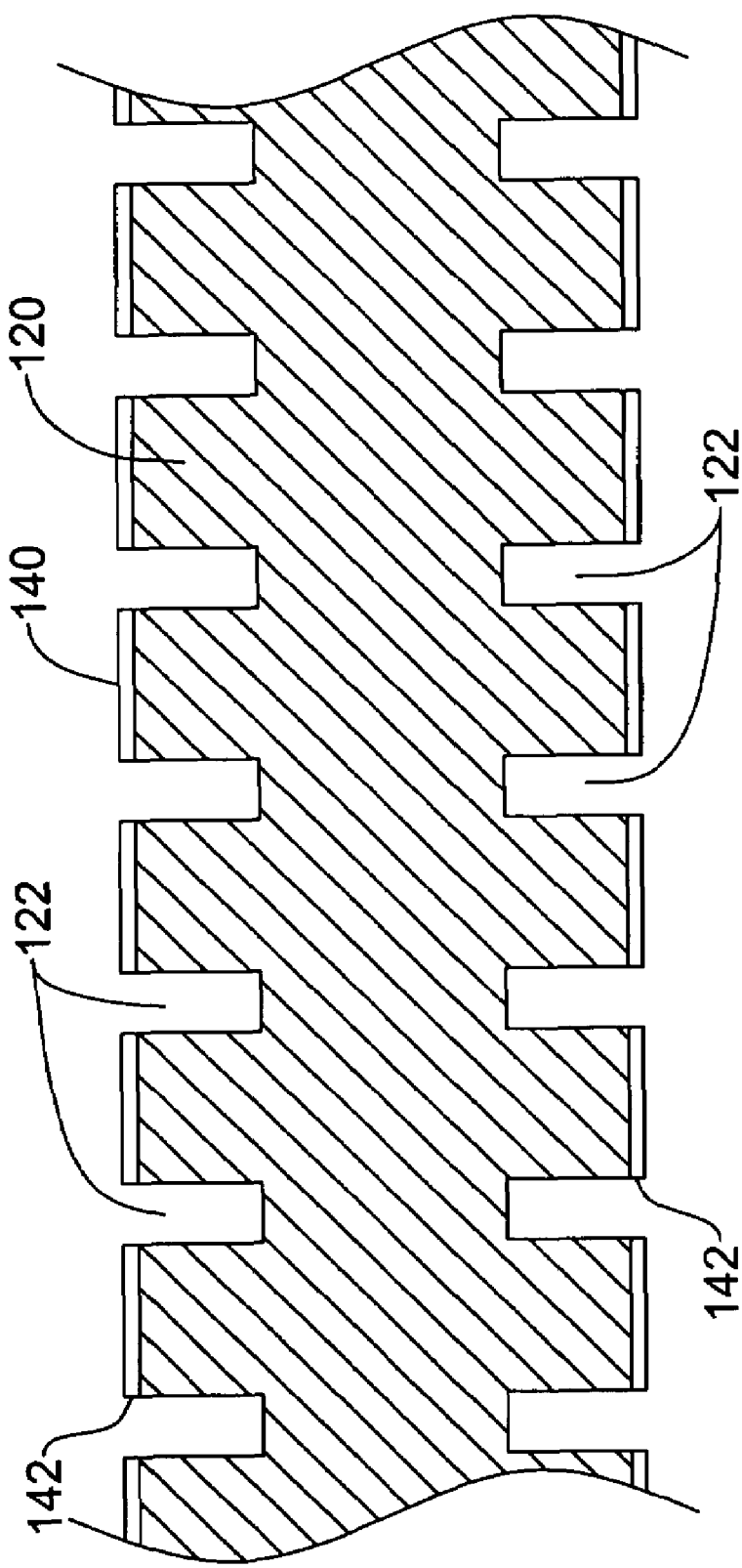
FIG. 8 is a cross-sectional view of a portion of an elongate medical device including an outer coating.

FIG. 8 is a cross-sectional view of a portion of the elongate member 120 of a guidewire shown in FIG. 7. As shown in FIG. 8, the elongate member 120 includes a coating 140 disposed on the outer surface 125 of the elongate member 120, or a portion thereof. The coating 140 is at least disposed on the outer surface 125 of a portion of the elongate member 120 including the plurality of apertures 122.

The coating 140 may include a plurality of openings 142 corresponding to the plurality of apertures 122 of the underlying portion of the elongate member 120. Thus, in some embodiments, the plurality of apertures 122 of the elongate member 120 are generally free of, unobstructed by, or otherwise not filled with the material forming the coating 140. By not filling the apertures 122 of the elongate member 120 with the coating material of the coating 140, the lateral flexibility of the portion of the elongate member 120 including the plurality of apertures 122 is not diminished.

Similar to the coating 40, the coating 140 may be a lubricious, a hydrophilic, a hydrophobic, a protective, a medicated, or other type of coating. The coating 140 may include, but is not limited to, any of the materials listed above regarding the coating 40, or other suitable coating materials known in the art. In disposing the coating material on the elongate member 120 to form the coating 140, the coating material may be dissolved, suspended in, or otherwise mixed with a solvent, such as, but not limited to, the solvents listed above.

Figure 9:
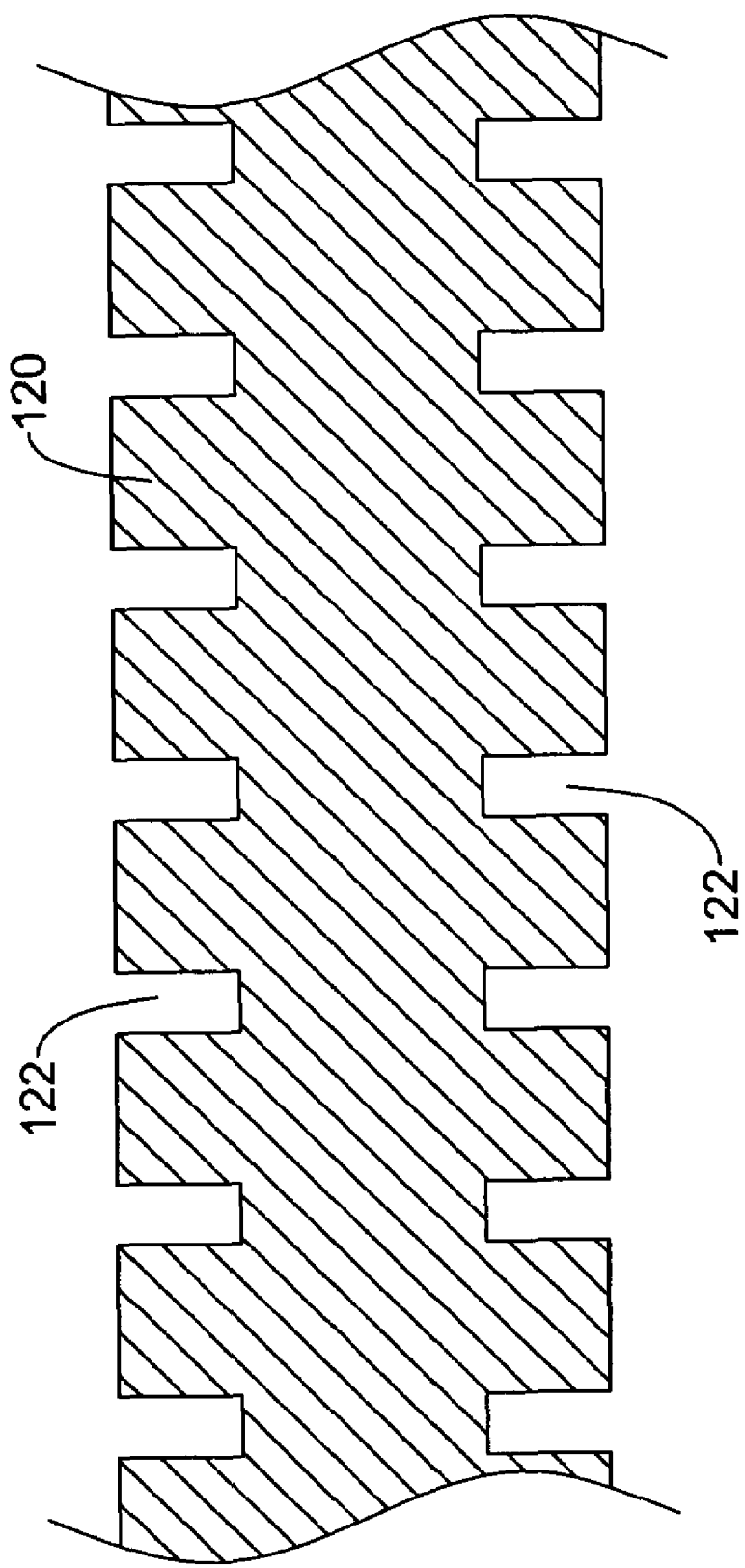
FIGS. 9-11 are cross-sectional views depicting an illustrative method of applying a coating to a portion of an elongate medical device.
Figure 10:
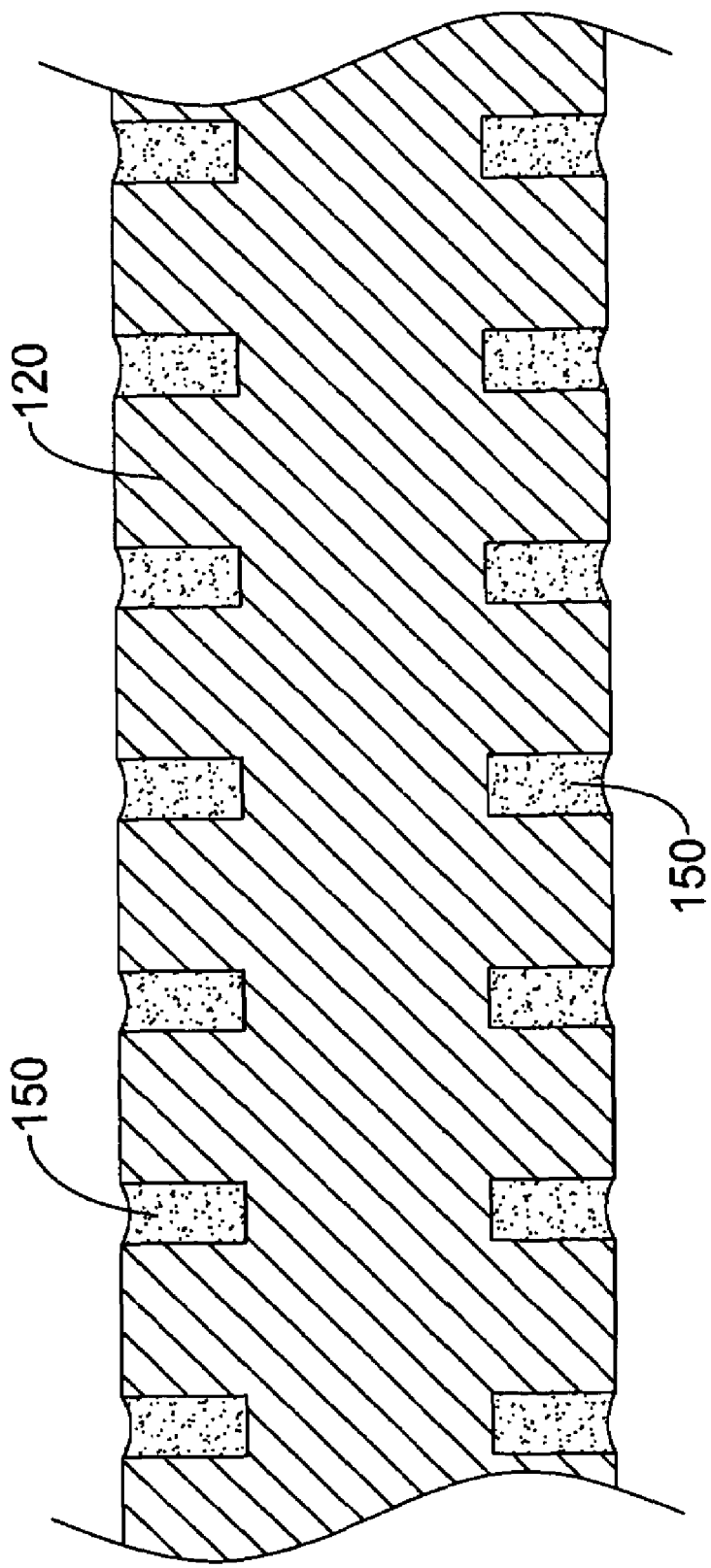

A similar method of applying the coating 140 onto the outer surface 125 of the elongate member 120 will now be discussed in connection with FIGS. 9-11. In FIG. 9, a portion of the elongate member 120 including a plurality of apertures 122 is shown absent a coating or outer layer. Now referring to FIG. 10, prior to applying the coating 140 to the elongate member 120, a removable liquid 150 may be disposed or dispensed in the plurality of apertures 122 of the elongate member 120, or a portion thereof. The removable liquid 150 may be disposed or dispensed in the apertures 122 in a variety of ways, such as by a dipping technique, a spraying technique, or a wiping technique, for example. The removable liquid 150 may be retained in the plurality of apertures 122 by surface tension and/or adhesive forces, for example.

In some embodiments, the removable liquid 150 may be a solvent, such as, but not limited to, the solvents listed above regarding the removable liquid 50. In some embodiments, it may be desirable that the solvent comprising the removable liquid 150 be the same as, or otherwise compatible with, the solvent utilized in the coating material solution, suspension, or mixture as described above.

Figure 11:
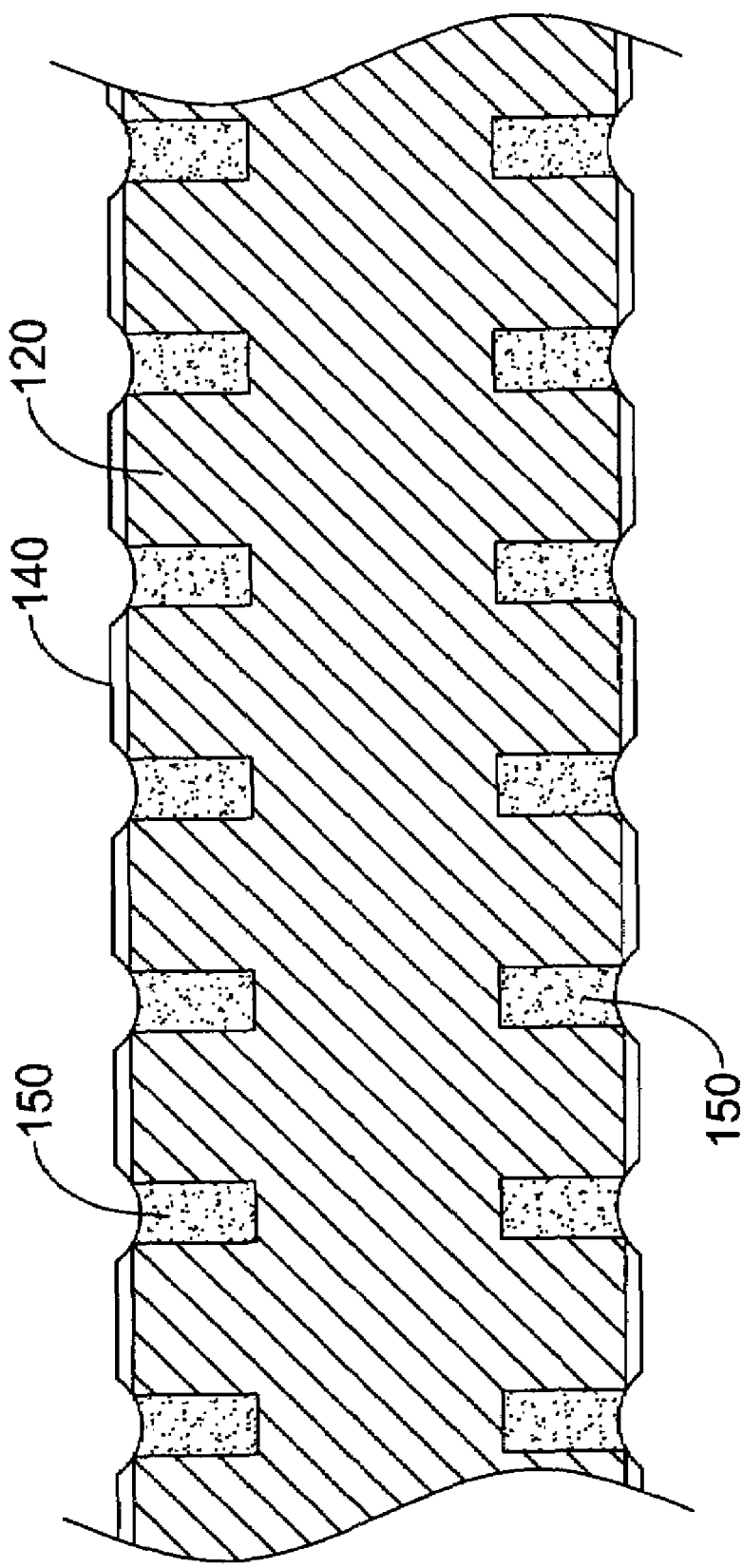

Now referring to FIG. 11, after the plurality of apertures 122 are filled with the removable liquid 150, the coating material forming the coating 140 may be applied to the elongate member 120. The coating material forming the coating 140 may be applied to the elongate member 120 by any of a variety of methods. For example, the coating material may be applied by spraying a solution or suspension of the coating material onto the elongate member 120, or the coating material may be applied by dipping the elongate member 120 into a solution or suspension of the coating material. In other embodiments, the coating 140 may be applied through an electro-coating process, an aqueous dispersion process, or a non-aqueous dispersion process, for example.

Because the plurality of apertures 122 are filled with the removable liquid 150 prior to the application of the coating 140, the coating material is generally prevented from entering, obstructing, and/or filling the plurality of apertures 122 of the elongate member 120. The coating material may provide a uniform coating 140 on the outer surface 125 of the elongate member 120, while leaving the plurality of apertures 122 free of, unobstructed by, or otherwise not filled with the coating material.

After the coating process is complete, the elongate member 120, or at least the portion of the elongate member 120 including the coating 140 may undergo a process of removing the removable liquid 150 from the apertures 122 and/or curing the coating 140. For, example, an oven (or other chamber used for heating and/or drying) may be used to cure the coating 140 and/or evaporate or dissipate the removable liquid 150. In some embodiments, evaporation operations may be conducted using a heating chamber suitable for maintaining an elevated temperature environment of between about 75° C. to about 110° C., for example. However, other temperature environments are possible. In some embodiments, ultraviolet (UV) light sources, or other radiation sources, may be used to cure the coating 40 and/or evaporate or dissipate the removable liquid 150. Alternatively, the removable liquid 150 may be removed from the apertures 122 by dissipation through natural evaporation (e.g. at room temperature) and/or expulsion such as with a vacuum or other expulsion means.

Subsequent to the removal of the removable liquid 150 from the plurality of apertures 122, the apertures 122 are free of, unobstructed by, or otherwise not filled with, the coating 140, as shown in FIG. 8. Thus, contrary to previous coatings which at least part fill, bridge, or otherwise partially or fully obstruct at least some of the apertures 122, the flexibility imparted on the elongate member 120 from the inclusion of the plurality of apertures 122 may be retained, yet the elongate member 120 may possess the benefits attributed to the inclusion of the coating 140.

Although the method of applying a coating to an elongate member including a plurality of apertures has been disclosed in association with a guidewire, it is not the intention to limit the disclosed method to guidewires. It is noted that the method of applying a coating may be adapted to apply a coating on an elongate shaft of a catheter or other similar elongate device.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of coating at least a portion of an elongate medical device, the method comprising the steps of:
   providing an elongate medical device having an outer surface, the elongate medical device including at least a portion having a plurality of apertures formed on the outer surface;
   dispensing a removable liquid in at least a portion of the plurality of apertures;
   coating at least a portion of the outer surface of the elongate medical device including the plurality of apertures filled with the removable liquid with a coating material; and removing the removable liquid from the plurality of apertures after the coating step.

2. The method of claim 1, wherein after removing the removable liquid from the at least a portion of the plurality of apertures, the plurality of apertures remain generally free of the coating material.

3. The method of claim 1, wherein after removing the removable liquid from the plurality of apertures, the plurality of apertures are generally unobstructed by the coating material.

4. The method of claim 1, wherein the coating material comprises silicone.

5. The method of claim 1, wherein the coating material comprises polytetrafluoroethylene (PTFE).

6. The method of claim 1, wherein the coating material comprises a hydrophilic polymer.

7. The method of claim 1, wherein the coating material comprises a hydrophobic polymer.

8. The method of claim 1, wherein the coating step includes a dip coating process.

9. The method of claim 1, wherein the coating step includes a spray coating process.

10. The method of claim 1, wherein the coating step includes an electro-coating process.

11. The method of claim 1, wherein the removable liquid is a solvent.

12. The method of claim 11, wherein the coating material includes a solvent, and wherein the solvent of the coating material is the same as the solvent of the removable liquid.

13. The method of claim 1, wherein the removable liquid is removed with a vacuum.

14. The method of claim 1, further comprising the step of subjecting the coating material to an elevated temperature environment to simultaneously cure the coating material and remove the removable liquid from the plurality of apertures.

15. A method of applying a coating to at least a portion of a medical guidewire, the method comprising the steps of:
providing a guidewire having an outer surface, wherein a portion of the guidewire includes a plurality of apertures extending inward from the outer surface;
filling at least a portion of the plurality of apertures with a removable liquid;
applying a coating to at least a portion of the guidewire including the plurality of apertures filled with the removable liquid; and
removing the removable liquid from the plurality of apertures after applying the coating, thereby maintaining the plurality of apertures generally free of the coating.

16. The method of claim 15, wherein the plurality of apertures remain unobstructed by the coating.

17. The method of claim 15, wherein the coating includes a plurality of openings corresponding to the plurality of apertures in the guidewire.

18. The method of claim 15, wherein the step of applying a coating includes a dipping process.

19. The method of claim 15, wherein the step of applying a coating includes a spraying process.

20. The method of claim 15, wherein the removable liquid comprises a solvent.

21. The method of claim 15, wherein the removable liquid is removed from the plurality of apertures by evaporation.

22. A method of coating at least a portion of an elongate medical device, the method comprising the steps of:
providing an elongate medical device having an outer surface, the elongate medical device including at least a portion having a plurality of apertures formed on the outer surface;
dispensing a removable liquid in at least a portion of the plurality of apertures;
coating at least a portion of the outer surface of the elongate medical device including the plurality of apertures filled with the removable liquid with a coating material; and
removing the removable liquid from the plurality of apertures after the coating step;
wherein the removable liquid is removed through evaporation.

23. The method of claim 22, wherein after removing the removable liquid from the at least a portion of the plurality of apertures, the plurality of apertures remain generally free of the coating material.

24. The method of claim 22, wherein after removing the removable liquid from the plurality of apertures, the plurality of apertures are generally unobstructed by the coating material.

25. The method of claim 22, wherein the removable liquid is a solvent.

26. The method of claim 25, wherein the coating material includes a solvent, and wherein the solvent of the coating material is the same as the solvent of the removable liquid.

27. The method of claim 22, wherein the removable liquid is removed with a vacuum.

28. The method of claim 22, further comprising the step of subjecting the coating material to an elevated temperature environment to simultaneously cure the coating material and remove the removable liquid from the plurality of apertures.

* * * * *